US011304708B2

(12) United States Patent
Alfonso et al.

(10) Patent No.: US 11,304,708 B2
(45) Date of Patent: Apr. 19, 2022

(54) ADJUSTABLE MICROFRACTURE HANDLE

(71) Applicant: Conmed Corporation, Utica, NY (US)

(72) Inventors: Gregory Alfonso, Largo, FL (US);
Robert A. Thibodeau, Saint Petersburg, FL (US); Matthew C. Summitt, Palm Harbor, NY (US)

(73) Assignee: Conmed Corporation, Utica, NY (US)

( * ) Notice: Subject to any disclaimer, the term of this patent is extended or adjusted under 35 U.S.C. 154(b) by 238 days.

(21) Appl. No.: 16/359,194

(22) Filed: Mar. 20, 2019

(65) Prior Publication Data

US 2019/0290294 A1 Sep. 26, 2019

Related U.S. Application Data

(60) Provisional application No. 62/735,390, filed on Sep. 24, 2018, provisional application No. 62/645,835, filed on Mar. 21, 2018.

(51) Int. Cl.
*A61B 17/16* (2006.01)
*A61B 17/17* (2006.01)

(52) U.S. Cl.
CPC ...... *A61B 17/1604* (2013.01); *A61B 17/1675* (2013.01); *A61B 17/1764* (2013.01); *A61B 17/1631* (2013.01); *A61B 17/1778* (2016.11)

(58) Field of Classification Search
CPC .......................... A61B 17/16–17/1604; A61B 17/1659–17/1695
See application file for complete search history.

(56) References Cited

U.S. PATENT DOCUMENTS

| | | | |
|---|---|---|---|
| 5,713,906 A * | 2/1998 | Grothues-Spork | ...... B25D 3/00 606/99 |
| 6,126,664 A | 10/2000 | Troxell et al. | |
| 6,764,491 B2 | 7/2004 | Frey et al. | |
| 7,060,072 B2 * | 6/2006 | Wolff | ................. A61B 17/1604 606/84 |
| 7,481,812 B2 | 1/2009 | Frey et al. | |
| 7,785,255 B2 | 8/2010 | Malkani | |
| 7,942,881 B2 * | 5/2011 | Torrie | ................ A61B 17/1675 606/86 R |
| 8,409,230 B2 | 4/2013 | Pamichev et al. | |
| 8,721,648 B2 | 5/2014 | Meridew | |
| 9,237,894 B2 | 1/2016 | Hernandez et al. | |
| 9,259,230 B2 * | 2/2016 | Rogers | ............... A61B 17/1604 |
| 9,393,030 B2 | 7/2016 | Meridew | |
| 9,398,918 B2 | 7/2016 | Torrie | |

(Continued)

*Primary Examiner* — Zade Coley
(74) *Attorney, Agent, or Firm* — Bond, Schoeneck & King, PLLC; Frederick J. M. Price

(57) ABSTRACT

A microfracture device for creating small holes in a bone. The microfracture device includes a handle having a body extending along a central longitudinal axis with a proximal end and a distal end; a shaft connected to the distal end of the body, the shaft having a distal tip; wherein the distal tip extends at first angle relative to the central longitudinal axis; a sliding mechanism slidably engaged with a surface of the body and moveable between a first configuration and a second configuration; and wherein the sliding mechanism further comprises a striking surface extending therefrom, wherein the striking surface is positioned at a second angle to the central longitudinal axis that is at least substantially similar to the first angle.

18 Claims, 16 Drawing Sheets

(56) References Cited

U.S. PATENT DOCUMENTS

| | | |
|---|---|---|
| 9,445,824 B2 | 9/2016 | Pamichev et al. |
| 9,655,630 B2 | 5/2017 | Hernandez et al. |
| 9,808,264 B2 | 11/2017 | Estes et al. |
| 9,968,365 B2 | 5/2018 | Torrie |
| 2007/0270870 A1* | 11/2007 | Torrie ................ A61B 17/1604 606/86 R |
| 2009/0143782 A1 | 6/2009 | Levi |
| 2010/0010546 A1 | 1/2010 | Hermida Ochoa |
| 2010/0318139 A1 | 12/2010 | Beauchamp |
| 2011/0106124 A1 | 5/2011 | Beauchamp |
| 2013/0237988 A1 | 9/2013 | Mauldin |
| 2013/0261626 A1 | 10/2013 | Chavarria et al. |
| 2014/0336656 A1* | 11/2014 | Rogers ................ A61B 17/1604 606/83 |
| 2016/0135862 A1 | 5/2016 | Shoshtaev |
| 2016/0374693 A1 | 12/2016 | Van Citters et al. |
| 2017/0215893 A1 | 8/2017 | Pamichev et al. |
| 2018/0161022 A1 | 6/2018 | Baboolal et al. |

* cited by examiner

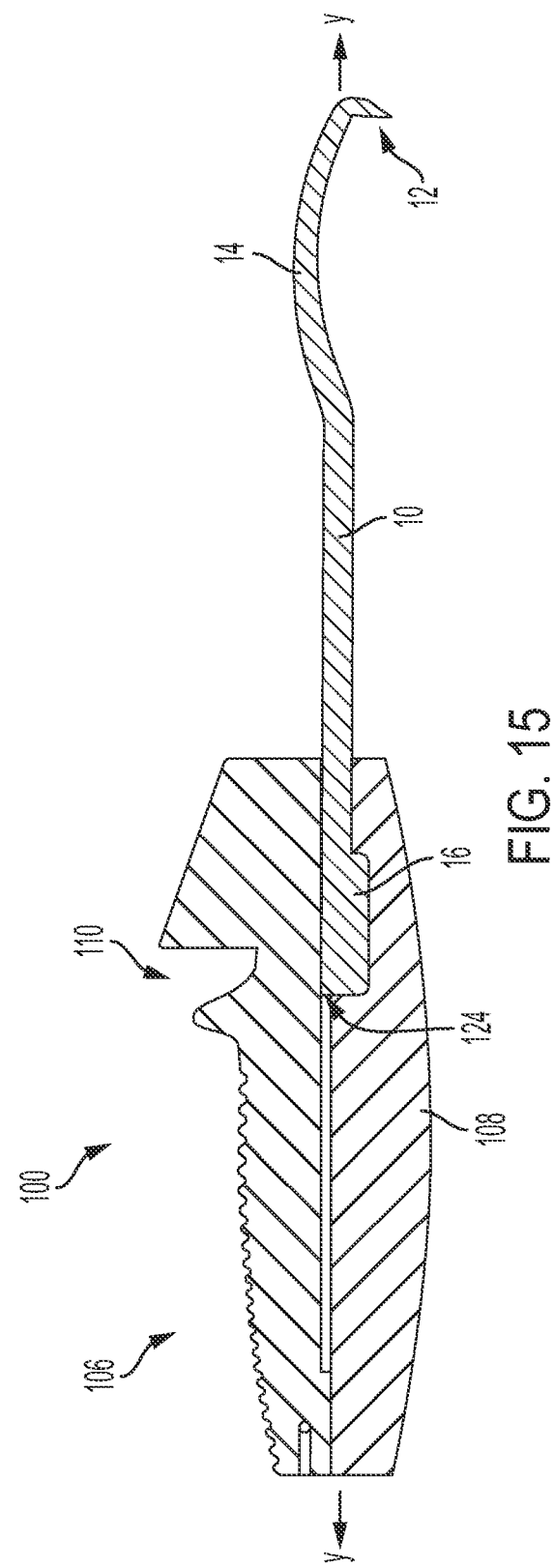

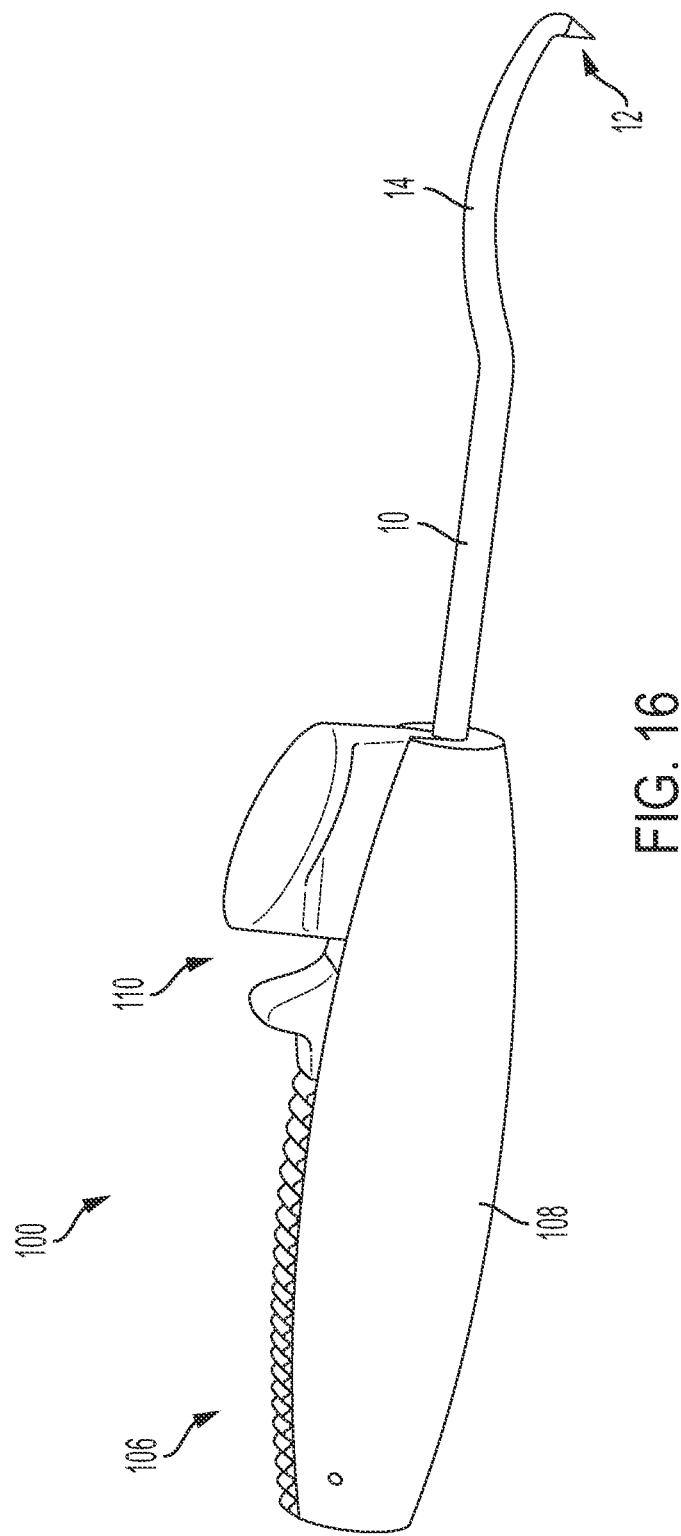

ADJUSTABLE MICROFRACTURE HANDLE

CROSS-REFERENCE TO RELATED APPLICATIONS

This application claims priority to U.S. Provisional Patent Application Ser. No. 62/645,835, filed on Mar. 21, 2018 and entitled "Adjustable Microfracture Handle" and U.S. Provisional Patent Application Ser. No. 62/735,390, filed on Sep. 24, 2018 and entitled "Adjustable Microfracture Handle (Modular/Disposable Design)," the entireties of which are incorporated herein by reference.

BACKGROUND OF THE INVENTION

1. Field of the Invention

The present invention is directed generally to surgical tools and instruments and, more particularly, to a microfracture awl for creating small holes in a bone.

2. Description of Related Art

A microfracture awl instrument is used to perform hip and knee microfracture techniques. Microfracture techniques include creating small fractures in bone to create a bleeding surface and promote the development of new cartilage. The creation of localized trauma using this technique has been shown to enhance chondral resurfacing by providing a suitable environment for new tissue formation, taking advantage of the body's own healing abilities. Conventional microfracture awls include a handle connected to a long shaft terminating in a distal tip. To create the small holes or fractures in the bone, a force must be applied to the shaft, which moves the distal tip into the bone. However, in current microfracture awls, the force is applied at or near the handle, which only applies a small fraction of the force at the distal tip.

In addition, the distal tip in conventional microfracture awls is positioned at a fixed angle relative to the bone. Thus, if a surgeon would like to adjust the angle at which the distal tip strikes the bone, the surgeon must manipulate the entire microfracture awl, placing it at a different angle. However, this it is difficult and sometimes impossible to adjust the angle of the entire microfracture awl when there is limited space at the surgical site. Therefore, in many instances, the surgeon must remove the current microfracture awl from the surgical site and replace it with a microfracture awl having a distal tip extending at a different, desired angle.

Therefore, there is a need for a microfracture awl with a mechanism for applying force near the distal tip and a mechanism for adjusting the angle at which the distal tip strikes the bone.

SUMMARY OF THE INVENTION

The present invention is directed to a microfracture device for creating small holes in a bone. According to one aspect, the microfracture device includes a handle having a body extending along a central longitudinal axis with a proximal end and a distal end, a channel extending through the body from the proximal end to the distal end (although, the channel does not need to extend fully from the proximal end to the distal end, it can extend from a position distal to the proximal end to the distal end), and a shaft connected to the distal end of the body. The shaft has a distal tip which extends at an angle relative to the central longitudinal axis. The microfracture device also includes a sliding mechanism movable within the channel between a first configuration and a second configuration. In the first configuration, the sliding mechanism is within the body of the handle and in the second configuration, the sliding mechanism is over at least a portion of the shaft. Alternatively, the body does not include a channel, and the sliding mechanism can be slidably engaged with the body (e.g., an outside surface thereof) by other means such as structurally surrounding the body, use of one or more grooves, etc. as should be appreciated by those of skill in the art in conjunction with a review of this disclosure.

According to another aspect, the microfracture device includes a handle having a body extending along a central longitudinal axis with a proximal end and a distal end, a channel extending through the body from the proximal end to the distal end, a cavity within the channel, a sliding mechanism movable within the channel over the cavity between a first configuration and a second configuration, and a shaft extending between a proximal raised portion and a distal tip, the proximal raised portion removably connected within the cavity in the channel. The distal tip extends at an angle relative to the central longitudinal axis.

According to another aspect, the present invention is a method for creating a microfracture, comprising the steps of: (i) providing a microfracture device with a handle having a body with a proximal end and a distal end, a channel extending through the body from the proximal end to the distal end, a shaft connected to the distal end of the body, the shaft having a distal tip, and a sliding mechanism movable within the channel between a first configuration and a second configuration, the sliding mechanism having a striking surface extending therefrom; (ii) inserting the microfracture device, in a first configuration, into a surgical site, wherein in the first configuration, the sliding mechanism is within the body of the handle; (iii) positioning the distal tip at a desired striking location on a bone, wherein the distal tip extends at an angle relative to the central longitudinal axis of the body or shaft; (iv) moving the sliding mechanism from the first configuration to a second configuration, wherein in the second configuration, the striking surface of the sliding mechanism is over at least a portion of the shaft; and (v) striking the striking surface, driving the distal tip into the bone.

In certain embodiments, the striking surface can be positioned at at least a substantially similar angle (and can be at an exact matching angle) as compared to the angle of the distal tip. The distal tip angle can be an angle relative to the central longitudinal axis of the body between 0 and 180 degrees (examples of which are shown and described in the accompanying figures).

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

FIG. 15 is a sectional side view schematic representation of the shaft within the cavity of the handle, according to an alternative embodiment; and FIG. 16 is a side perspective view schematic representation of a microfracture device, according to an alternative embodiment.

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
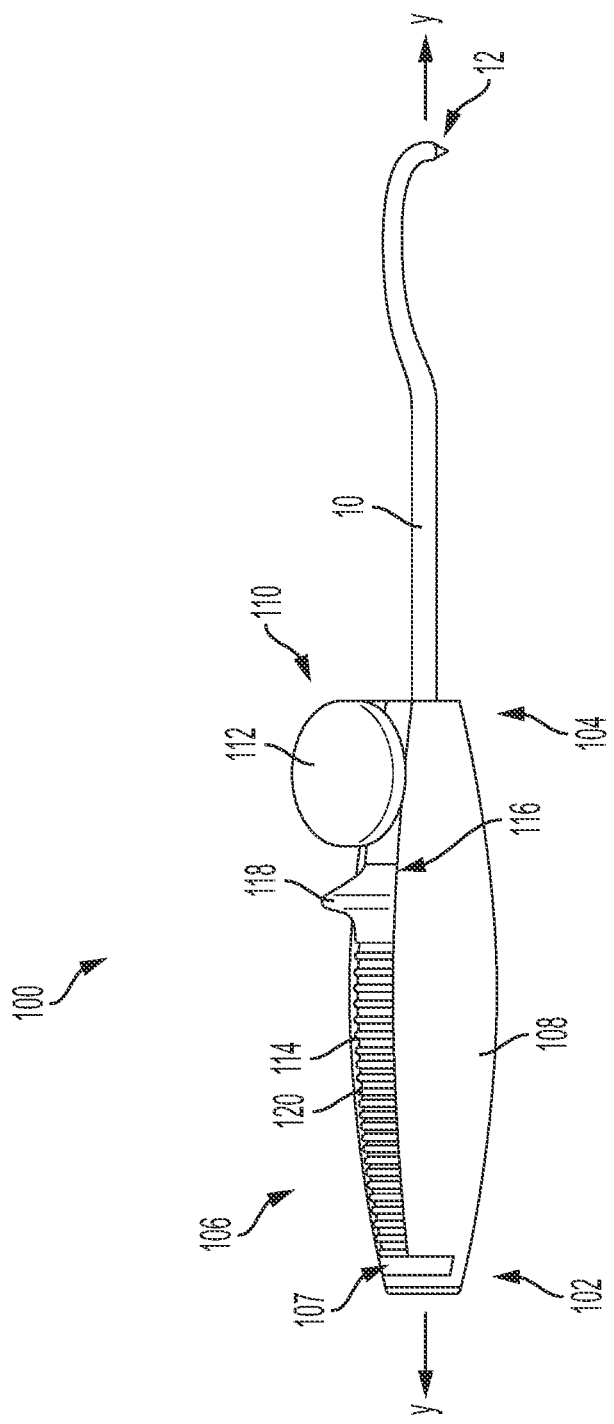
FIG. 1 is a top perspective view schematic representation of a microfracture device in a first configuration, according to an embodiment.

Referring now to the figures, wherein like reference numerals refer to like parts throughout, FIG. 1 shows a top perspective view schematic representation of a microfracture awl (hereinafter "microfracture device") 100 in a first configuration, according to an embodiment. The microfracture device 100 comprises a proximal handle 106 having a body 108. The body 108 of the microfracture device 100 has a proximal end 102 and a distal end 104 extending along a central longitudinal y-y axis. The microfracture device 100 also comprises a sliding mechanism 110 which is movable along the body 108 of the handle 106. In the embodiment shown in FIG. 1, the body 108 comprises a handle backstop 107 that restricts the sliding mechanism 110 from moving farther in the proximal direction from the first configuration shown. In an alternative embodiment, a pin (not shown) extends through the body 108 at the proximal end 102 and similarly restricts the sliding mechanism 110 from moving farther in the proximal direction from the first configuration shown in FIG. 1. The distal end 104 of the body 108 of the handle 106 is connected to a shaft 10 extending to a distal tip 12.

Still referring to FIG. 1, the sliding mechanism 110 comprises a striking surface 112 (which can be positioned at or adjacent to the distal end of the sliding mechanism, but does not have to be). The purpose of the striking surface 112 is to receive force to drive the distal tip 12 toward a substrate, such as a bone or cartilage. For example, a surgeon can mallet the striking surface 112, which applies force on the shaft 10, driving the distal tip 12 into a bone or cartilage. In the depicted embodiment, the striking surface 112 is circular or round to apply force radially and equally in all directions on the shaft 10 of the microfracture device 100. Although a round striking surface 112 is shown in FIG. 1, any shape and configuration can be used. In the depicted embodiment, the striking surface 112 is parallel to the central longitudinal y-y axis and perpendicular to the plane in which the distal tip 12 extends to ensure that all the striking force is more precisely directed to drive the distal tip 12 into the bone and not in any direction that could cause the distal tip 12 to bend or scrape along the surface of the bone or surrounding cartilage.

The sliding mechanism 110 shown in FIG. 1 also comprises an elongated portion 114, which is a rod-like structure. The elongated portion 114 extends proximally from the striking surface 112 within a channel 116 (FIG. 2) of the body 108 of the handle 106 (alternatively, the channel can be within the elongated portion 114 and a portion of the body 108 can extend within that channel). In the depicted embodiment, the elongated portion 114 is at least partially within the channel 116 in the body 108 of the handle 106. The elongated portion 114 can also comprise a distal thumb rest 118. In FIG. 1, the thumb rest 118 is a projection or protrusion that extends away from the body 108 of the handle 106. The thumb rest 118 is adjacent the striking surface 112 and is used to push the sliding mechanism 110 (in the distal direction with the striking surface 112). The thumb rest 118 also ensures that the thumb of the surgeon is clear from malleting at the striking surface 112 for safety. The elongated portion 114 can also have a plurality of external ridges 120, such as those shown in FIG. 1. The ridges 120 can be on the elongated portion 114 in the proximal direction from the thumb rest 118. The ridges 120 provide a grip for the surgeon to assist in moving the sliding mechanism 110 along the shaft 10.

Figure 2:
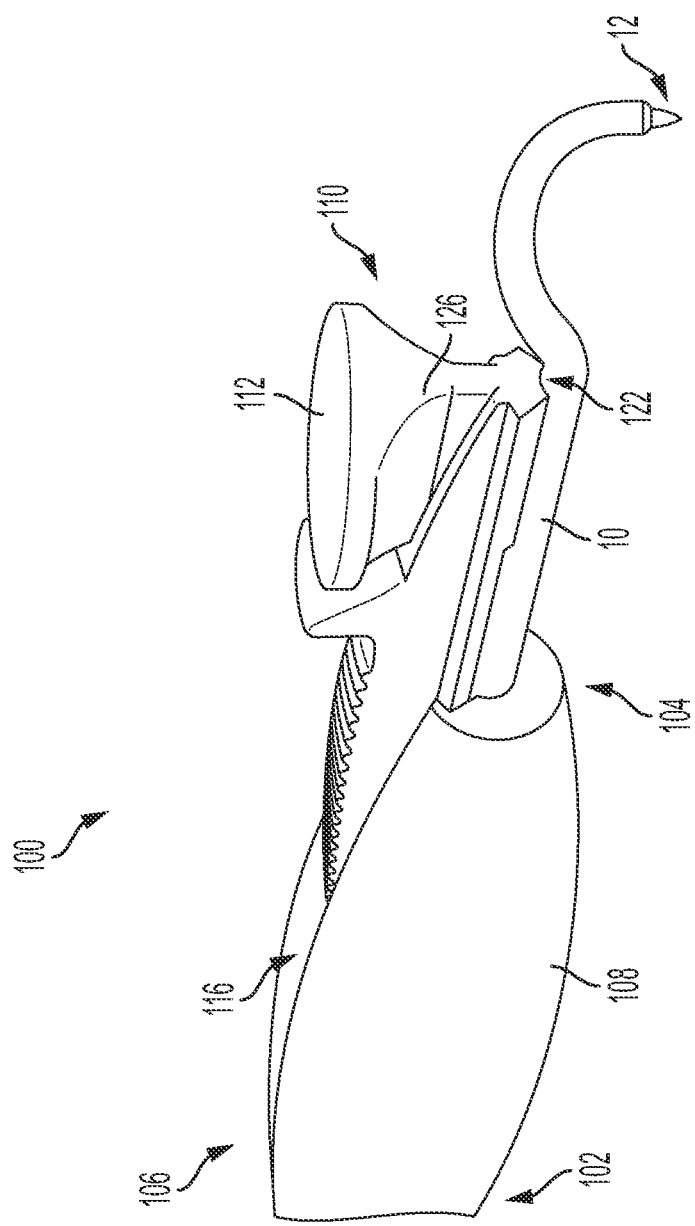
FIG. 2 is a side perspective view schematic representation of the microfracture device in a second configuration, according to an embodiment.

Turning now to FIG. 2, there is shown a side perspective view schematic representation of the microfracture device 100 in a second configuration, according to an embodiment. The sliding mechanism 110 is configured to move along the shaft 10 from the first configuration, shown in FIG. 1, to the second configuration, shown in FIG. 2. In the depicted embodiment, the sliding mechanism 110 is movable along the shaft 10 in the distal direction toward the distal tip 12 and back in the proximal direction toward the proximal end 102 of the body 108 of the handle 106. The mobility of the sliding mechanism 110 allows the surgeon to keep the striking surface 112 as close to the distal tip 12 as possible, while allowing for variation in patient size. In the depicted embodiment, the striking surface 112 will stay perpendicular to the distal tip 12 regardless of its position along the shaft 10.

As shown in FIG. 2, the striking surface 112 extends to a striking body 126 with a rectangular cross-section (although any other shaped cross-sections can be used). In the depicted embodiment, the sliding mechanism 110 comprises a groove (or track) 122 sized and configured to fit partially around the shaft 10 such that the sliding mechanism 110 can move along the shaft 10. In the depicted embodiment, the striking surface 112 is on an opposing side of the striking body 126 as the groove (or track) 122. The sliding mechanism 110 contacts the shaft 10 directly underneath striking surface 112 to ensure that the force from the strike is applied as closely to the distal tip 12 as possible.

Figure 3:
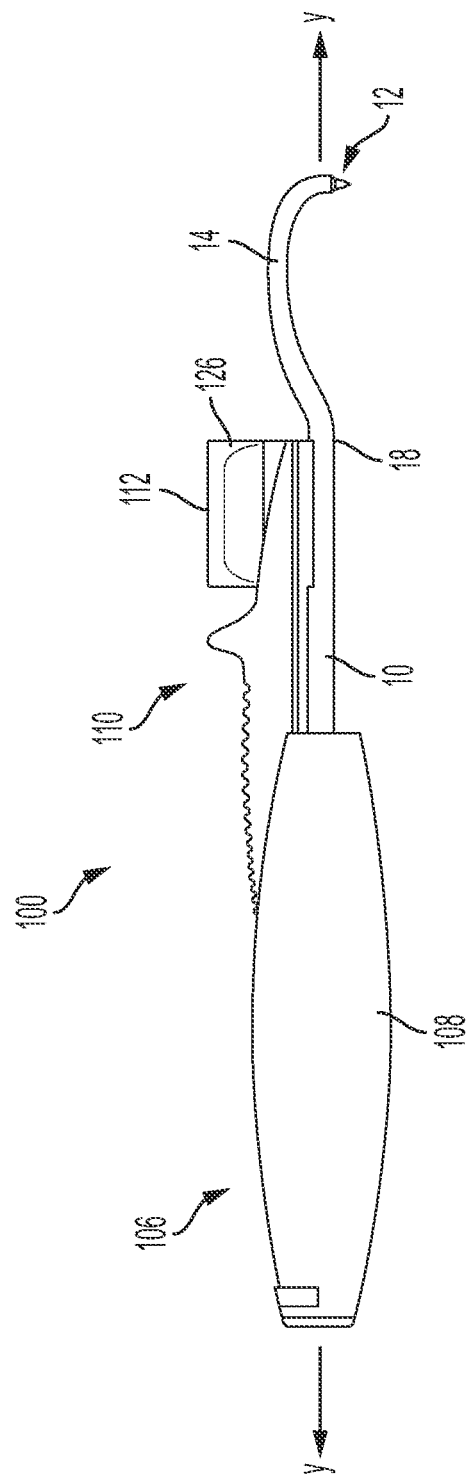
FIG. 3 is a side view schematic representation of the microfracture device in the second configuration, according to an embodiment.

Referring now to FIG. 3, there is shown a side view schematic representation of the microfracture device 100 in the second configuration, according to an embodiment. In the depicted embodiment, the shaft 10 comprises a distal curved portion 14 connected to the distal tip 12. The curved portion 14 can be an attachment to the shaft 10 or formed in the same material as the shaft 10. Further, boundaries of the curved portion 14 can be delineated. For example, a proximal end 16 of the curved portion 14 can be indicated by a marking along the shaft 10 or a seam 18 where the curved portion 14 connects to the shaft 10. In the depicted embodiment, the proximal end 16 of the curved portion 14 also marks the farthest distance that the sliding mechanism 110 can move in the distal direction. In other words, the sliding mechanism 110 cannot move beyond the shaft 10 to the curved portion 14. In an embodiment not shown, the curved portion 14 has a diameter larger than that of the shaft 10, which prevents the sliding mechanism 110 from moving to the curved portion 14. Alternatively, the sliding mechanism 110 can move onto the curved portion 14.

Still referring to FIG. 3, as mentioned above, the curved portion 14 extends to the distal tip 12 of the microfracture device 100. In the depicted embodiment, the curved portion 14 is curved such that the distal tip 12 is at a 90° angle relative to the central longitudinal y-y axis. In use, the surgeon moves the sliding mechanism 110 from the first configuration (shown in FIG. 1) wherein the sliding mechanism 110 is entirely within the body 108 of the handle 106 in the distal direction to the second configuration (shown in FIG. 3) wherein the sliding mechanism 110 is fully extended to the curved portion 14 (or to any partially extended position or non-extended position as may be appropriate for the specified use, as should be appreciated by a person of skill in the art in conjunction with a review of this disclosure). The surgeon can then mallet the striking surface 112, driving the distal tip 12 downward toward a substrate (not shown), such as a bone. Although only first and second configurations are shown, the surgeon can extend the sliding mechanism 110 to any point therebetween (i.e., any point along the shaft 10 between the distal end 104 of the body 108 and the curved portion 14).

Figure 4:
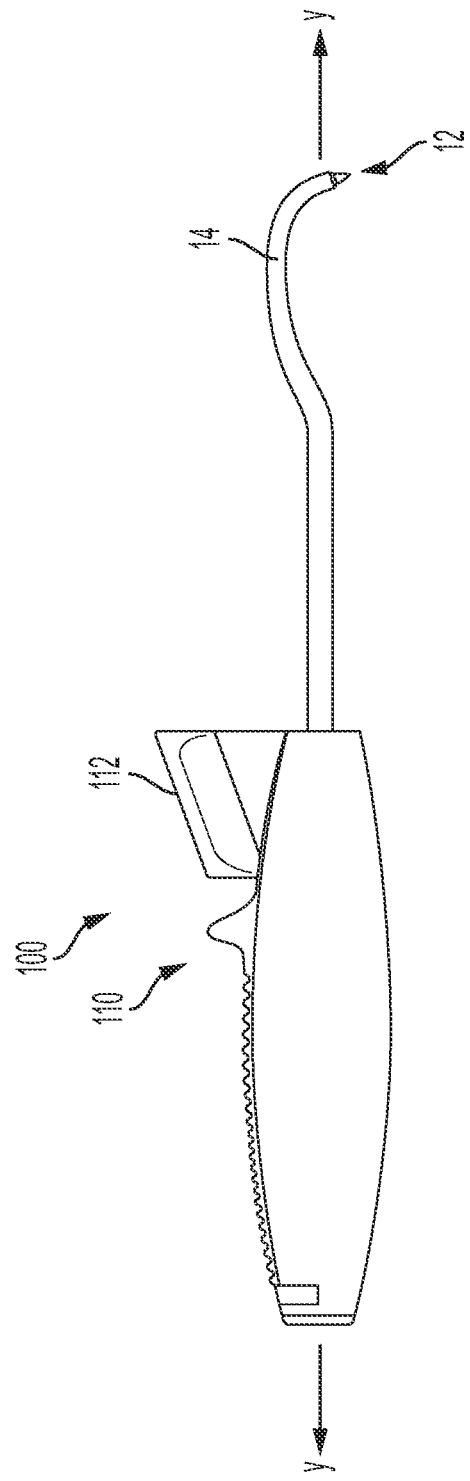
FIG. 4 is a side view schematic representation of the microfracture device in the first configuration, according to an alternative embodiment.
Figure 5:
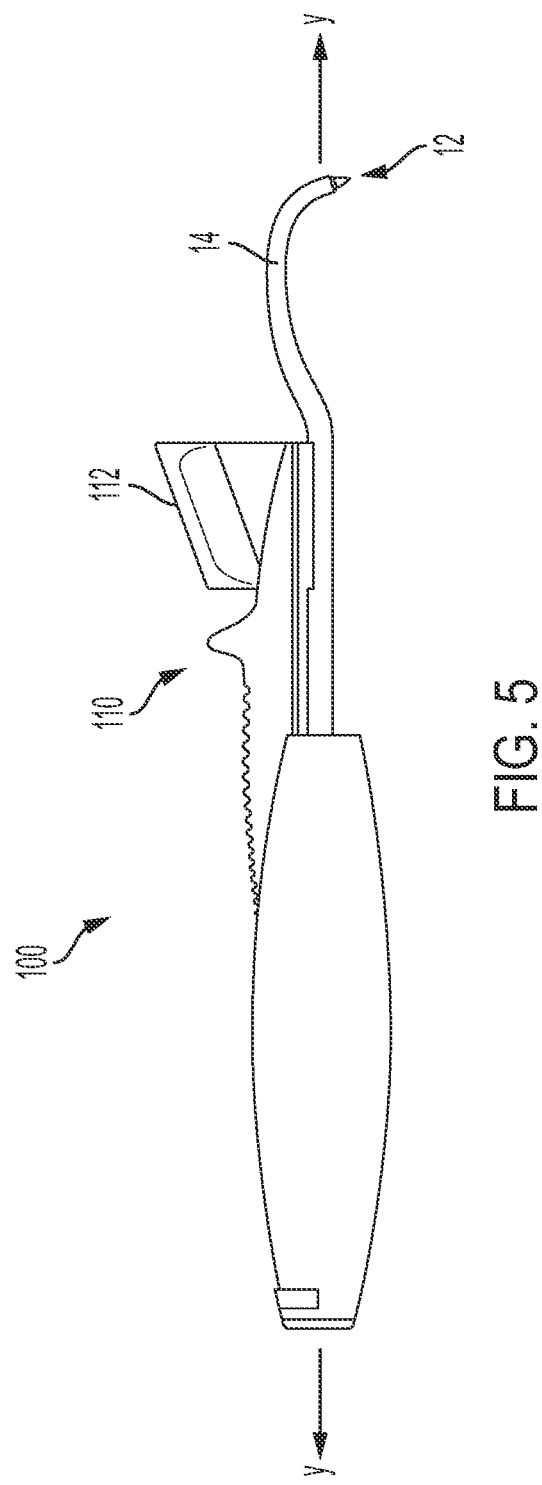
FIG. 5 is a side view schematic representation of the microfracture device in the second configuration, according to an alternative embodiment.

Turning now to FIGS. 4 and 5, there are shown side views schematic representations of the microfracture device 100, according to an alternative embodiment. In the depicted embodiment, the curved portion 14 is curved differently than the embodiment of the microfracture device 100 shown in FIGS. 1-3. In the embodiment shown in FIGS. 4-5, the curved portion 14 is curved such that the distal tip 12 is at a 70° angle relative to the central longitudinal y-y axis. In other words, when a surgeon (or other user) mallets the striking surface 112, force drives the distal tip 12 into a substrate, such as a bone or cartilage, at a 70° angle if the substrate is parallel to the central longitudinal y-y axis. As also shown in FIGS. 4-5, the striking surface 112 is at a 70° angle relative to the central longitudinal y-y axis. Matching the angle of the striking surface 112 with the angle of the distal tip 12 ensures that force is applied perpendicular to the distal tip 12 so that shaft 10 does not bend and more precisely directing the desired force to the distal tip 12.

Figure 6:
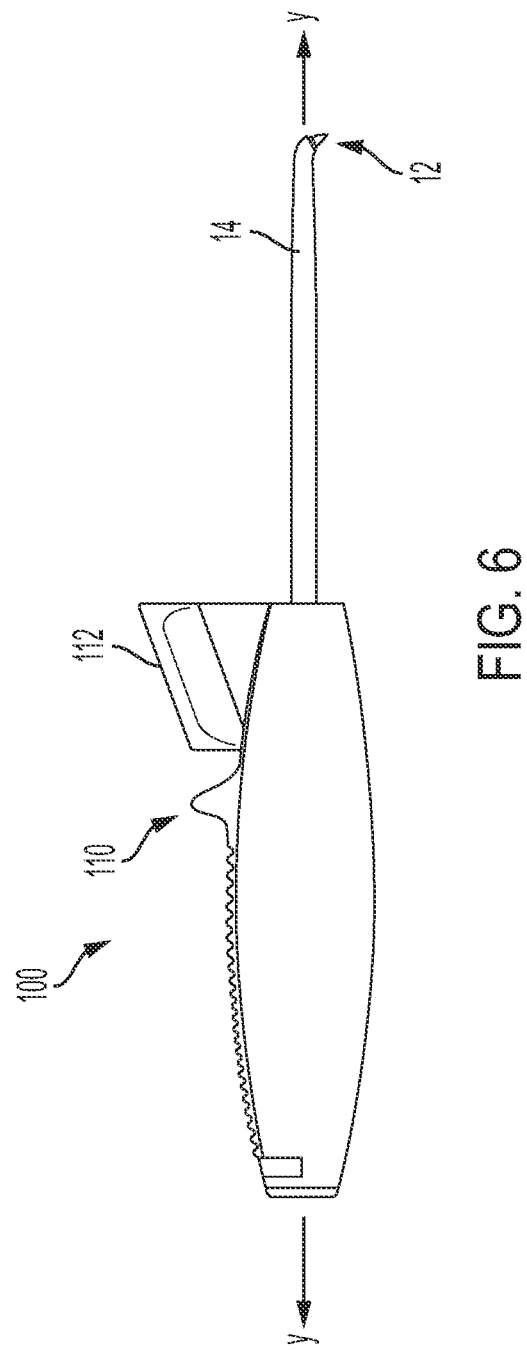
FIG. 6 is a side view schematic representation of the microfracture device in the first configuration, according to another embodiment.
Figure 7:
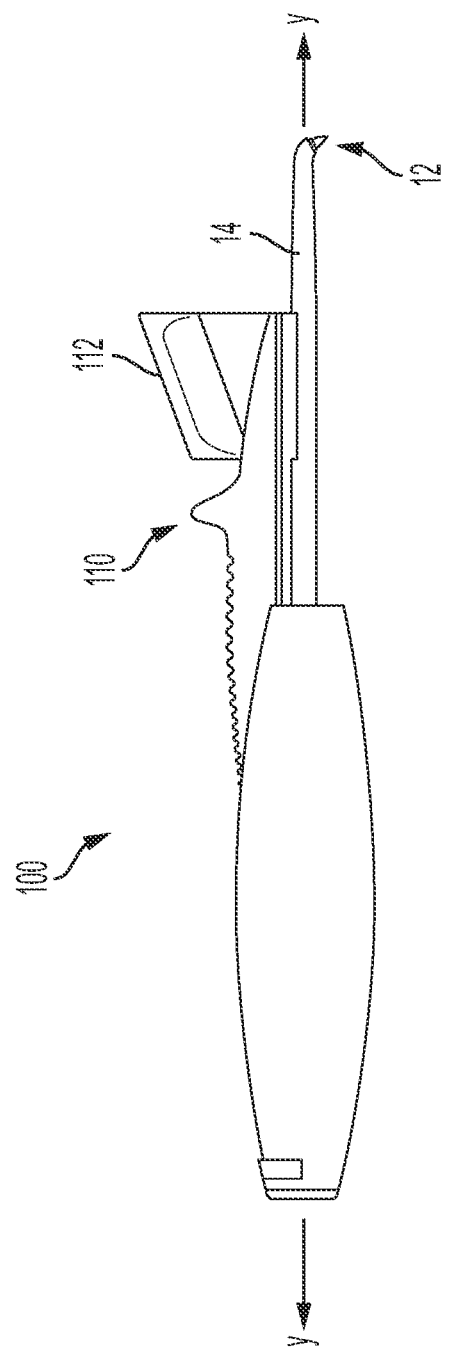
FIG. 7 is a side view schematic representation of the microfracture device in the second configuration, according to another embodiment.

Referring now to FIGS. 6 and 7, there are shown side views schematic representations of the microfracture device 100, according another embodiment. In the depicted embodiment, the curved portion 14 is slightly less curved or angled as compared to the curved portions 14 of the embodiments of the microfracture device 100 in FIGS. 1-5. In the embodiment shown in FIGS. 6-7, the curved portion 14 is curved such that the distal tip 12 is at a 60° angle relative to the central longitudinal y-y axis. In other words, when a surgeon (or other user) mallets the striking surface 112, force drives the distal tip 12 into a substrate, such as a bone or cartilage, at a 60° angle if the substrate is parallel to the central longitudinal y-y axis. As also shown in FIGS. 6-7, the striking surface 112 is at a 60° angle relative to the central longitudinal y-y axis to match the angle of the striking surface 112 with the angle of the distal tip 12 and ensure that force is applied perpendicular to the distal tip 12.

Figure 8:
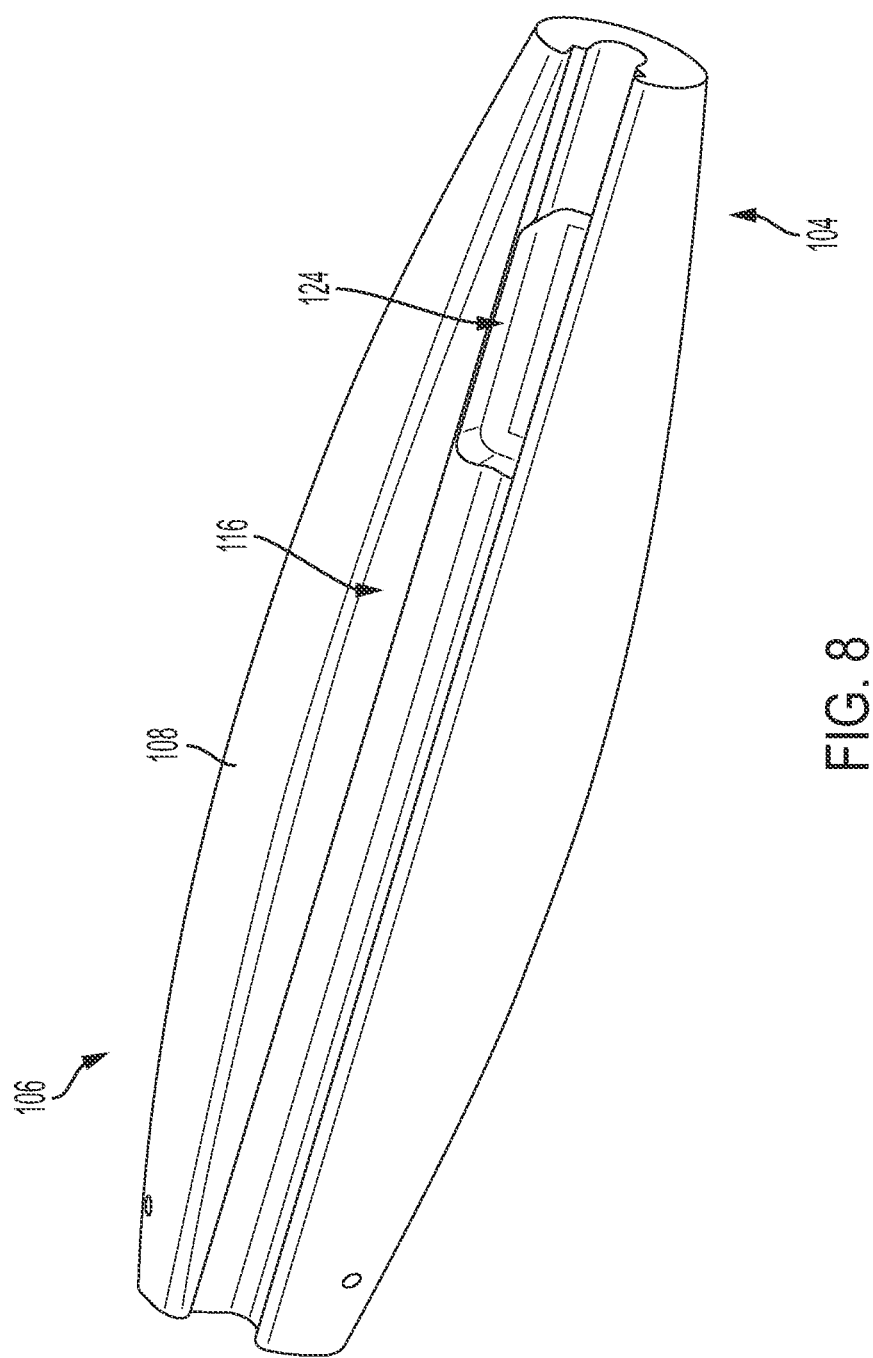
FIG. 8 is a top perspective view schematic representation of the body of the handle, according to an alternative embodiment.

Turning now to FIG. 8, there is shown a top perspective view schematic representation of the body 108 of the handle 106, according to an alternative embodiment. The channel 116 extending through the body 108 of the handle 106 can be seen in FIG. 8. As described above, the channel 116 is sized and configured for the sliding mechanism 110 to move in the proximal and distal directions therethrough. The body 108 of the handle 106 shown in FIG. 8 additionally comprises a cavity 124 within the channel 116. In the depicted embodiment, the cavity 124 is in a distal end 104 of the body 108.

Figure 9:
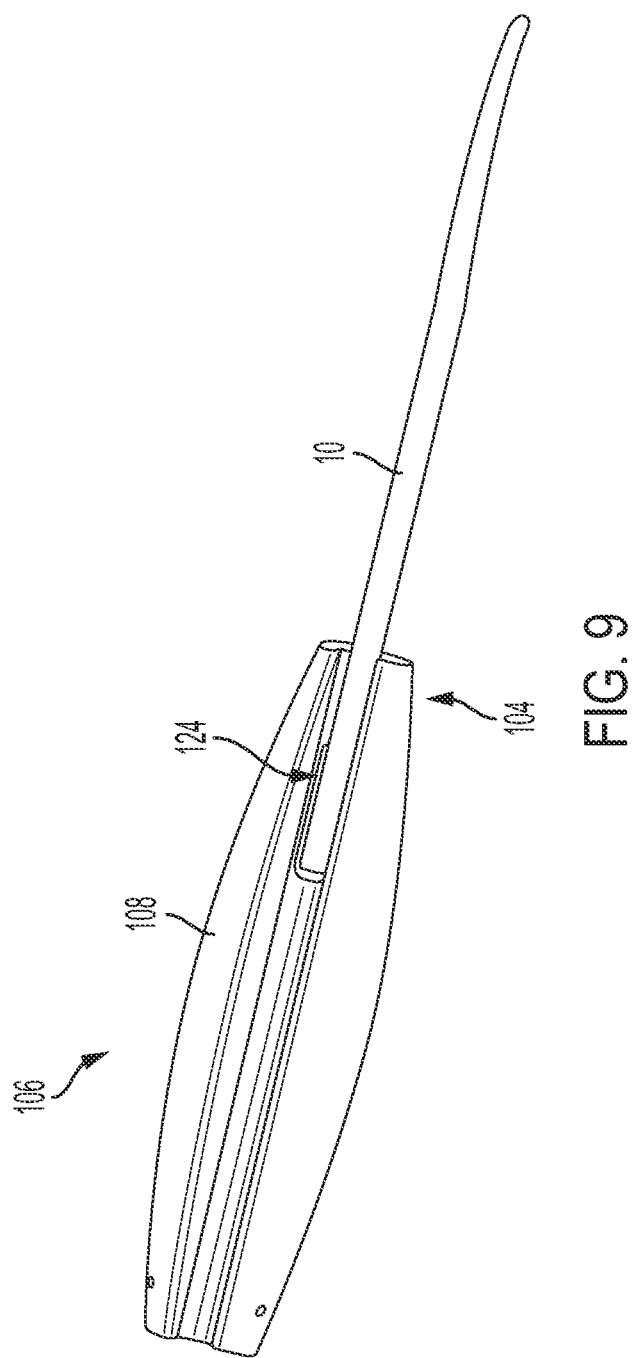
FIG. 9 is a top perspective view schematic representation of a shaft within the cavity of the handle (with the sliding mechanism removed), according to an embodiment.
Figure 10:
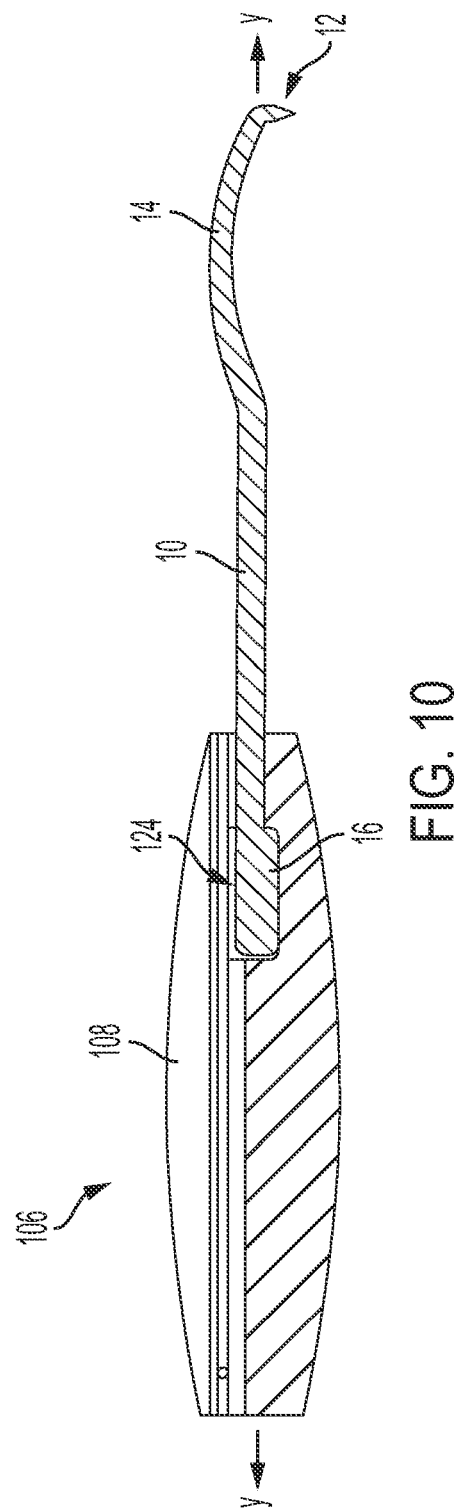
FIG. 10 is a sectional side view schematic representation of a shaft within the cavity of the handle (with the sliding mechanism removed), according to an embodiment.

Referring now to FIGS. 9 and 10, there are shown top perspective and sectional side views schematic representations of a shaft 10 within the cavity 124 of the handle 106 (with the sliding mechanism 110 removed), according to an embodiment. As shown in FIG. 9, the shaft 10 is sized and configured to fit within the cavity 124 in the distal end 104 of the body 108 of the handle 106. In particular, as shown in FIG. 10, the shaft 10 comprises a raised portion 16 (or other protrusion) that is sized and configured to fit within the cavity 124. In the depicted embodiment, the raised portion 16 is rectangular; however, the raised portion 16 can be a protrusion of any size or shape as long as it fits within the cavity 124. The purpose of the raised portion 16 is to restrict the shaft 10 from moving rotationally, proximally or distally within the body 108 of the handle 106, while making the shaft 10 removable from the handle 106.

In the embodiments depicted in FIGS. 9 and 10, the curved portion 14 of the shaft 10 is curved such that the distal tip 12 is at a 90° angle relative to the central longitudinal y-y axis (and a substrate (not shown) if the substrate is parallel to the central longitudinal y-y axis). As also shown in FIGS. 9-10, the striking surface 112 is at a 90° angle relative to the central longitudinal y-y axis (as also shown in FIG. 1-3) to match the angle of the striking surface 112 with the angle of the distal tip 12 and ensure that force is applied perpendicular to the distal tip 12.

Figure 11:
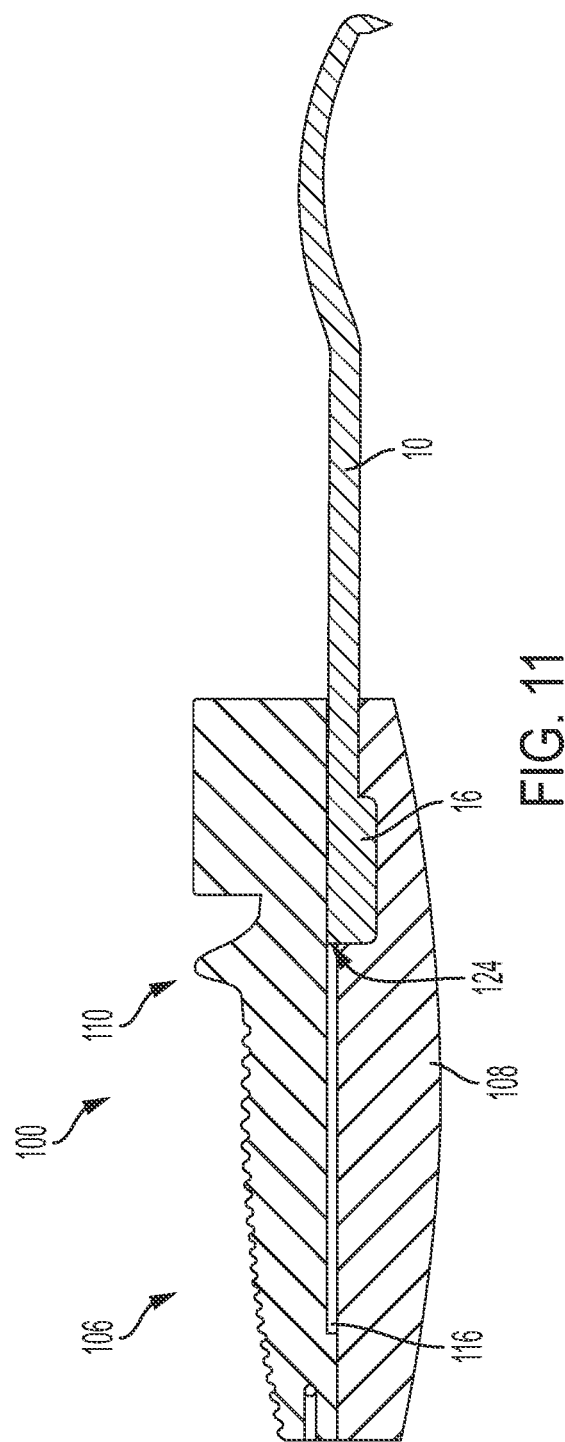
FIG. 11 is a sectional side view schematic representation of a shaft within the cavity of the handle (including the sliding mechanism), according to an embodiment.
Figure 12:
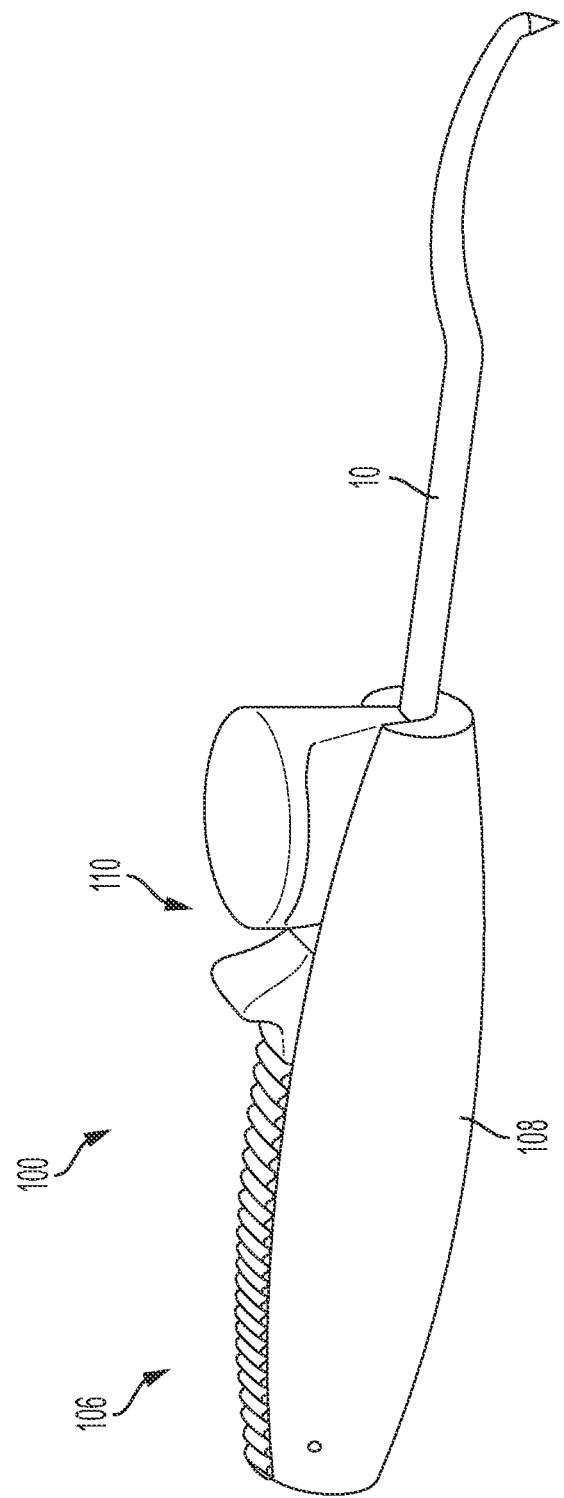
FIG. 12 is a side perspective view schematic representation of a microfracture device, according to an embodiment.
Figure 13:
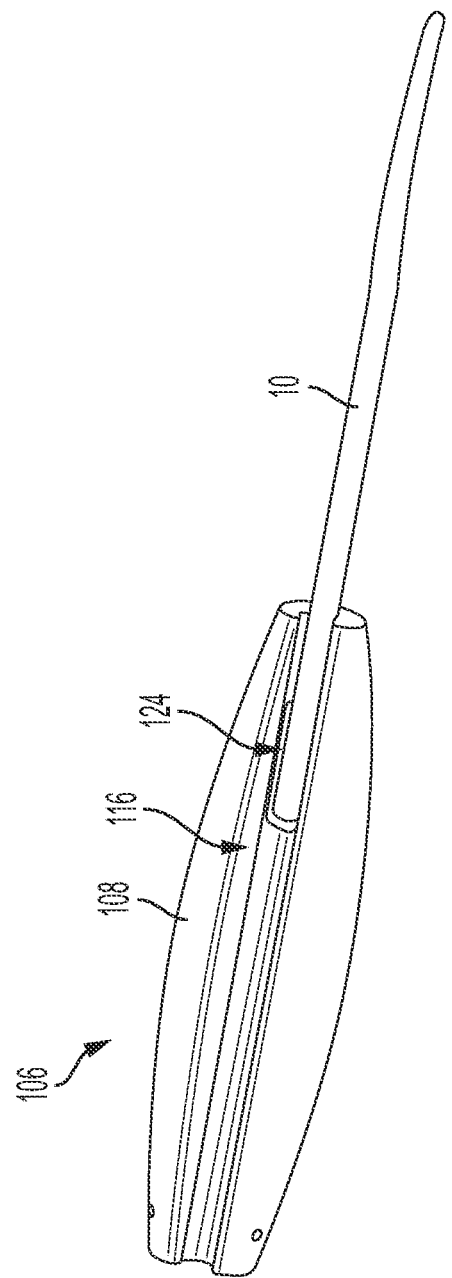
FIG. 13 is a top perspective view schematic representation of a shaft within the cavity of the handle (with the sliding mechanism removed), according to an alternative embodiment.
Figure 14:
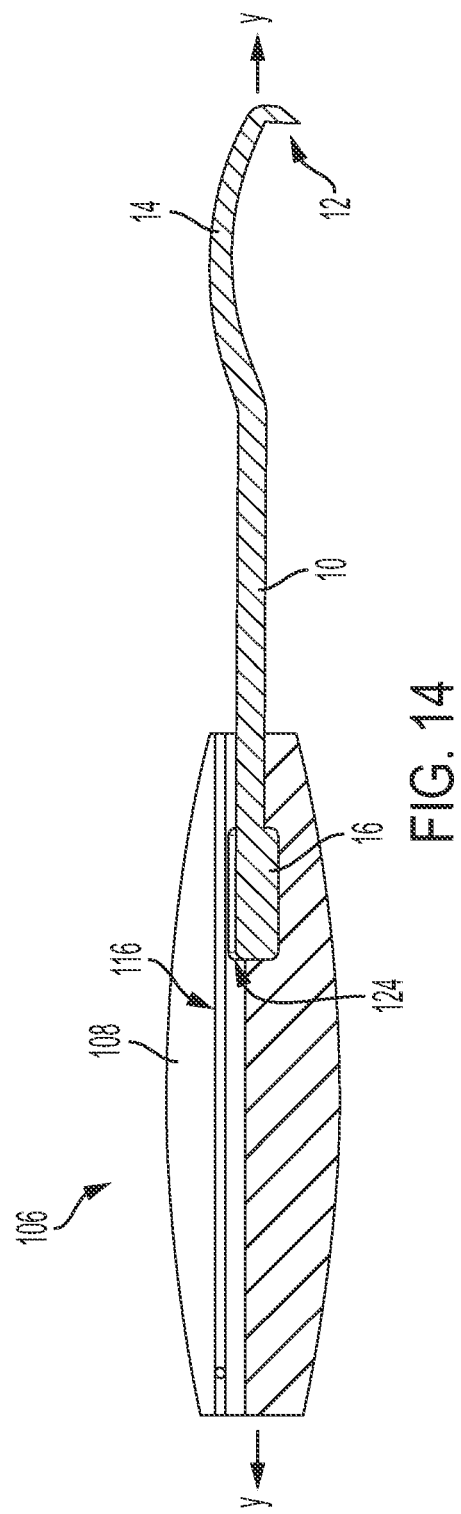
FIG. 14 is a sectional side view schematic representation of the shaft within the cavity of the handle (with the sliding mechanism removed), according to an alternative embodiment.

Turning now to FIGS. 11 and 12, there are shown top perspective and sectional side views schematic representations of a shaft 10 within the cavity 124 of the handle 106, according to an embodiment. In the depicted embodiment, the sliding mechanism 110 of the microfracture device 100 is shown within the channel 116 of the body 108 of the handle 106. As shown in FIGS. 11 and 12, the sliding mechanism 110 is within the channel 116 over the cavity 124 containing the raised portion 16 of the shaft 10. The sliding mechanism 110 prevents the raised portion 16 of the shaft 10 from moving upward and out of the cavity 124 in the body 108 of the handle 106 while still allowing the sliding mechanism 110 to move along the shaft 10.

Referring now to FIGS. 13-16, there are shown various views schematic representations of a shaft 10 within the cavity 124 of the handle 106, according to an alternative embodiment. The shaft 10 in FIGS. 11 and 12 can be removed and replaced with the shaft 10 in FIGS. 13 and 14. The shaft 10 in FIGS. 13-16 also comprises a raised portion 16 which is sized and configured to fit within the cavity 124 such that the shaft 10 of FIGS. 11 and 12 can be removed and replaced with the shaft 10 of FIGS. 13-16. To remove the shaft 10 from the body 108 of the handle 106, the sliding mechanism 110 is moved in the proximal direction to a third configuration, exposing the channel 116 above the cavity 124. With the sliding mechanism 110 removed, the raised portion 16 of the shaft 10 can be pulled out of the cavity 124 and the shaft 10 can be removed from the handle 106.

In the embodiments depicted in FIGS. 13-16, the curved portion 14 of the shaft 10 is curved such that the distal tip 12 is at a 110° angle relative to the central longitudinal y-y axis (and a substrate (not shown) if the substrate is parallel to the central longitudinal y-y axis). As shown in FIGS. 15-16, the striking surface 112 is at a 110° angle relative to the central longitudinal y-y axis. Matching the angle of the striking surface 112 with the angle of the distal tip 12 ensures that force is applied perpendicular to the distal tip 12 so that shaft 10 does not bend. The ability to interchange shafts 10 with distal tips 12 extending at different angles (and matching these distal tips 12 with matching angled striking surfaces 112) allows a surgeon to choose a shaft 10 with a distal tip 12 to match the anatomy of a specific joint. Interchangeability of shafts 10 also lends to disposable or replaceable shafts 10. Thus, a shaft 10 can be replaced when it has lost performance due to wear from use, and/or for biosafety reasons.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments can be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but can also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A microfracture device, comprising:
    a handle having a body extending along a central longitudinal axis with a proximal end and a distal end;
    a shaft connected to the distal end of the body, the shaft having a distal tip;
    wherein the distal tip extends at first angle relative to the central longitudinal axis;
    a sliding mechanism slidably engaged with a surface of the body, the sliding mechanism fits over and partially around and is movable with respect to an outside surface of the shaft between a first configuration and a second configuration; and
    wherein the sliding mechanism further comprises a striking surface extending therefrom, wherein the striking surface is positioned at a second angle to the central longitudinal axis that is at least substantially similar to the first angle.

2. The microfracture device of claim 1, wherein the sliding mechanism also comprises an elongated portion extending proximally from the striking surface.

3. The microfracture device of claim 2, wherein in the first configuration, a portion of the sliding mechanism is within the body of the handle and in the second configuration, a portion of the sliding mechanism is positioned over at least a portion of the shaft.

4. The microfracture device of claim 3, further comprising a thumb rest positioned along the elongated portion, the thumb rest located proximally relative to the striking surface.

5. The microfracture device of claim 2, wherein the striking surface is circular.

6. The microfracture device of claim 5, further comprising a striking body extending from the striking surface, the striking body having a rectangular cross-section.

7. The microfracture device of claim 1, wherein the shaft further comprises a curved portion proximally adjacent to and extending to the distal tip.

8. The microfracture device of claim 7, wherein in the second configuration, the distal sliding mechanism is positionable up to the curved portion of the shaft.

9. The microfracture device of claim 1, wherein the distal tip extends at an angle equal to or less than 90° relative to the central longitudinal axis.

10. The microfracture device of claim 9, wherein the distal tip extends at a 90° angle relative to the central longitudinal axis.

11. The microfracture device of claim 1, wherein the distal tip extends at an angle greater than 90° relative to the central longitudinal axis.

12. The microfracture device of claim 11, wherein the distal tip extends at a 110° angle relative to the central longitudinal axis.

13. A microfracture device, comprising:
   a handle having a body extending along a central longitudinal axis with a proximal end and a distal end;
   a channel extending through the body from the proximal end to the distal end;
   a cavity within the channel;
   a sliding mechanism movable within the channel over the cavity between a first configuration and a second configuration;
   a shaft extending between a proximal raised portion and a distal tip, the proximal raised portion removably connected within the cavity in the channel; and
   wherein the sliding mechanism fits over and partially around and is moveable with respect to an outside surface of the shaft, and the distal tip extends at an angle relative to the central longitudinal axis.

14. The microfracture device of claim 13, wherein the distal tip extends at an angle equal to or less than 90° relative to the central longitudinal axis.

15. The microfracture device of claim 13, wherein the distal tip extends at an angle greater than 90° relative to the central longitudinal axis.

16. The microfracture device of claim 13, wherein the sliding mechanism comprises an elongated portion extending proximally from a striking surface.

17. The microfracture device of claim 16, wherein sliding mechanism is movable to a third configuration where the sliding mechanism extends from the proximal end of the body, exposing the cavity within the channel.

18. The microfracture device of claim 13, wherein in the first configuration, the sliding mechanism is positioned within the body of the handle and in the second configuration, the sliding mechanism is positioned over at least a portion of the shaft.

* * * * *